United States Patent
L'abbé et al.

(10) Patent No.: US 9,359,487 B2
(45) Date of Patent: Jun. 7, 2016

(54) PLASTICIZERS BASED ON MIXED ESTERS OF SUCCINATE

(71) Applicant: Proviron Holding N.V., Hemiksem (BE)

(72) Inventors: Marc L'abbé, Hemiksem (BE); Garrett Minne, Hemiksem (BE)

(73) Assignee: PROVIRON HOLDING N.V., Hemiksem (BE)

( * ) Notice: Subject to any disclaimer, the term of this patent is extended or adjusted under 35 U.S.C. 154(b) by 0 days.

(21) Appl. No.: 14/424,629

(22) PCT Filed: Aug. 27, 2013

(86) PCT No.: PCT/BE2013/000043
§ 371 (c)(1),
(2) Date: Feb. 27, 2015

(87) PCT Pub. No.: WO2014/040146
PCT Pub. Date: Mar. 20, 2014

(65) Prior Publication Data
US 2015/0225537 A1    Aug. 13, 2015

(30) Foreign Application Priority Data

Aug. 28, 2012 (BE) .................................. 2012/0562

(51) Int. Cl.
C08K 5/11    (2006.01)
C08L 27/06   (2006.01)
C08K 5/12    (2006.01)
C08K 5/00    (2006.01)

(52) U.S. Cl.
CPC ... *C08K 5/12* (2013.01); *C08K 5/11* (2013.01); *C08K 5/0016* (2013.01); *C08L 27/06* (2013.01)

(58) Field of Classification Search
CPC .......... C08K 5/0016; C08K 5/11; C08L 27/06
See application file for complete search history.

(56) References Cited

U.S. PATENT DOCUMENTS

| | | | | |
|---|---|---|---|---|
| 2,136,436 A * | 11/1938 | Haught | ................ | C03C 27/10 106/169.37 |
| 2,689,865 A * | 9/1954 | Dazzi | ................ | C07C 69/40 524/287 |
| 2,905,651 A * | 9/1959 | Reid et al. | ................ | 524/114 |
| 3,148,207 A * | 9/1964 | Weinkauff | ................ | C08K 5/10 524/296 |
| 3,483,247 A * | 12/1969 | Mills | ................ | 560/85 |
| 4,243,571 A * | 1/1981 | Gabbard | ................ | C08K 5/11 524/287 |
| 4,313,866 A * | 2/1982 | Renshaw | ................ | 524/287 |
| 4,343,652 A * | 8/1982 | Allart et al. | ................ | 106/31.2 |
| 8,313,838 B2 * | 11/2012 | Steuer | ................ | B32B 17/10761 426/437 |
| 2015/0111036 A1* | 4/2015 | Chaudhary | ................ | C08K 5/11 428/375 |
| 2015/0114263 A1* | 4/2015 | Facklam | ................ | 106/505 |

FOREIGN PATENT DOCUMENTS

| | | | | |
|---|---|---|---|---|
| EP | 0013167 A1 | 7/1980 | | |
| EP | 2 631 266 A1 * | 8/2013 | ............ | C08K 5/11 |
| FR | 2026170 A1 * | 9/1970 | ............ | C08F 29/00 |
| GB | 1071525 | 6/1967 | | |
| JP | 2003-082158 A | 3/2003 | | |
| WO | WO 2013/124318 A1 * | 8/2013 | ............ | C08K 5/11 |

OTHER PUBLICATIONS

Stuart, Amanda et al. "Poly(vinyl chloride) plasticized with succinate esters: synthesis and characterization." Polym. Bull. (2010) 65: pp. 589-598.

International Search Report and Written Opinion of the International Searching Authority, mailed on Nov. 7, 2013, from counterpart International Application No. PCT/BE2013/000043, filed on Aug. 27, 2013.

International Preliminary Report on Patentability, mailed on Mar. 3, 2015, from counterpart International Application No. PCT/BE2013/000043, filed on Aug. 27, 2013.

* cited by examiner

*Primary Examiner* — Rip A Lee

(74) *Attorney, Agent, or Firm* — HoustonHogle LLP

(57) ABSTRACT

The present invention relates to plasticizers for use in a thermoplastic polymer. The plasticizers according to the invention comprise a succinate mixed ester of benzyl on the one part and branched nonyl or decyl on the other part. According to a preferred embodiment the molar amount of mixed ester in the plasticizer amounts to at least 30%. The invention also relates to plastisoles comprising such plasticizers.

15 Claims, No Drawings

PLASTICIZERS BASED ON MIXED ESTERS OF SUCCINATE

The present application is the U.S. national phase of International Application No. PCT/BE2013/000043, filed on Aug. 27, 2013.

FIELD OF THE INVENTION

This invention relates to a new composition of a mixed ester of succinic acid—succinic acid ester or succinate—that can be used as a plasticiser. More in particular the invention relates to a mixed succinate ester resulting from the esterification of succinic acid with on the one hand benzyl alcohol and on the other hand branched alcohols with nine or ten carbon atoms, branched nonyl or decyl alcohol. These products have specific properties relating to a quick fusing or jellifying action.

Also the choice of the alcohols and the succinic acid yields products of fully or partially biological origin. By virtue hereof they help to enhance the ecological durability of the end application.

BACKGROUND OF THE INVENTION

Polyvinylchloride (PVC) is a technically and economically very important polymer and is used as soft PVC and hard PVC in a large number of applications. For soft PVC plasticisers are often used. Important applications include amongst others electrical isolation materials around cables, flooring materials, various coating applications and shoe soles.

Plasticisers are used in various polymers to enhance the flexibility. By virtue hereof the possibilities and applications of these polymers are substantially enhanced. Plasticisers usually are liquids that can be used in various technical processes. They are optimized for various polymers. More in particular the polarity of a plasticiser should match with the polarity of the polymer to obtain a good interaction with the highest efficiency and low migration. Plasticisers are used in various polymers, among which the most important are: polyvinylchloride, polyamide, polar rubbers and polyurethane. Also in PVC plasticisers are often used. An important field of applications are those whereby the PVC is suspended in the plasticiser and a plastisole is being formed that can be coated on a substrate. On this substrate heating it above the so-called jellifying temperature then jellifies the PVC layer. For this application good and quick jellifying plasticisers (e.g. fast fusers) are used. They lower the jellifying temperature of PVC. Traditional examples of these products are for example BBP (benzyl-butyl-phthalate) or ethyleneglycol-propyleneglycol di-benzoate.

Plasticisers for polymers are usually phtallic acid esters. Still today about 80% of the plasticisers for PVC are phthalates. They give the product an enhanced flexibility in a great number of applications. The plasticiser molecules are positioned among the polymer chains and enhance the mobility of the polymer chains and lower the glass transition temperature. Plasticisers have the ability to couple substantially improved process properties to a high flexibility of the end product. The working principle of the above plasticisers relate to the so-called external plasticisers.

These are products that additionally are added to polymers after their preparation; their plasticiser function is a result of a physical interaction with the polymer molecules, as described above.

There also exist internal or inside plasticisers. These are products that during the preparation of the polymers in the polymer chain are incorporated as copolymers and by virtue hereof give the end product a flexible property. The present invention only relates to so-called external plasticisers.

Esters are the most interesting class of plasticisers. Apart from the earlier mentioned phthalate esters, also amongst others the following plasticisers are often found in actual applications: adipates, sebacates, maleates, gluterates, trimellitates, citrates, benzoates, sulfonamides, phosphate-esters, glycoletheresters, terephthalates, cyclohexane-dicarboxylates and polymeric plasticisers. Recently more plasticisers are being developed and used, partly or entirely synthesized from biological raw materials. Examples of the latter are: citrate esters, epoxied oils or fatty acid esters, acetylated monoglycerides.

The most often used plasticisers are di-octyl-phthalate (DOP), di-2-ethylhexylphtalate (DEHP), di-isononylphtalate (DiNP), di-isodecylphthalate (DiDP), di-undecylphthalate (DiUP), di-2-ethylhexyladipate (DOA), acetyl-tributylcitrate (ATBC), di-isononyl-cyclohexane-1,2-dicarboxylate (DINCH), di-octyl-terephthalate (DOTP).

Also esters of succinic acid or succinates are known as potential plasticisers.

In most applications the di-esters are used, that result from the esterification of succinic acid with a single aliphatic alcohol (both alkoxy groups being the same).

STUART et all. have published an article on this subject 'Poly (vinyl chloride) plasticised with succinate esters: synthesis and characterization', published in Polym. Bull. (2010). In this case they used di-octyl-succinate (DOSu), di-hexyl-succinate (DHSu), di-butyl-succinate (DBSu) and di-ethyl-succinate (DESu). They observed various parameters such as infrared absorption and glass transition temperature and compared these results with di-octyl-phthalate (DOP). However the plasticisers that had been tested were characterised by a substantially higher volatility (VOC, volatile organic compound) compared to the standard plasticisers as phthalates and comparable adipates. So from a commercial and technical point of view they are of less relevancy. From test results performed by the present inventors it appears that di-2-ethylhexyl-succinate (DEHSu) is approximately twice as volatile as the comparable adipate ester, di-2-ethylhexyladipate (DEHA).

Tests performed by the present inventors also revealed that the normal aliphatic di-esters of succinic acid with 2 equal alkoxygroups either exhibit a too high volatility or an insufficient jellifying property as desired for typical applications.

In the known state of the art plasticisers are also described that can be obtained by esterification of succinic acid with a mixture of two different types of alcohols. In this way a mixture can be obtained of products comprising an ester of succinic acid with two different alkoxygroups.

Reference is made for example to the British patent specification Nr. 1,071,525, filed Aug. 31, 1964, calling upon a priority of a Swiss application filed Aug. 29, 1963. This patent has been published on Jun. 7, 1967, applicant is Lonza Ltd.

This application describes the plasticising effect on amongst others vinyl chloride polymers with low-molecular weight esters based on succinic acid compounds. As an example on page 2, left column, line 43, is mentioned lauryloxy-propylene-succinoyldioxy-propylene acetate.

This is a mixed ester of succinic acid with at both sides an alkyl rest, at the one side with 15 carbon atoms, at the other side with 5 carbon atoms.

Nowhere in the text the use of these compounds in plastisoles has been described.

Reference is also made to the U.S. Pat. No. 3,483,247, filed on Nov. 9, 1964, published and issued on Dec. 9, 1969, in the name of Monsanto Co., St. Louis, USA.

This application describes on column 1, lines 30-32 the preparation of an aliphatic benzyl ester, being an ester comprising on the one side a benzyl group and on the other side an aliphatic group.

Column 4, line 1-2, cites the use of these products as plasticiser in vinyl halide plastics.

Column 4, line 45, cites succinic anhydride as starting raw material.

Column 4, lines 71 and following cite examples of monohydroxy aliphatic alcohols.

Amongst others are cited 2-ethylhexyl alcohol, nonyl alcohol, decyl alcohol, dodecyl alcohol, tridecyl alcohol, . . . .

Specific mixed esters based on succinic acid are mentioned in column 7, lines 33-35: benzyl methyl/ethyl/isohexyl succinates, so a mixed ester with benzyl on the one side, and on the other side an alkyl with 1, 2, 6 carbon atoms, and also: benzyl 2 ethylhexyl, so with 8 carbon atoms, and further benzyl decyl succinate: so with 10 carbon atoms; and further also benzyl tridecyl succinate . . . so with 13 carbon atoms. The text does not mention any specific properties of the cited succinate plasticisers.

Further reference is being made to the U.S. Pat. No. 3,148,207, filed on Apr. 14, 1958, issued on Sep. 8, 1964, in the name of Monsanto Co., Delaware, USA. This application describes the use of plasticisers for polyvinylchloride (column 1, lines 16-17).

Column 2 cites a long enumeration of carbonic acids that upon esterification may serve as plasticisers. Line 26 mentions succinic acid.

Column 3, line 72 mentions the use of mixed esters.

In example 14 on column 8 the preparation of a symmetric succinic acid ester has been described, namely dioctyldecyl succinate.

Further reference is made to the Japanese patent publication with publication number 2003 082158.

This application is published on Mar. 19, 2003, applicant is Arakawa Chem. Ind. Co Ltd., Japan.

This application mentions the use of a very specific succinate, namely on the basis of ditetrahydrofurfuryl as plasticiser for biologically degradable polyesters.

Further reference is being made to the European Patent Application Nr. 0013 167, filed on Dec. 21, 1979, calling upon a priority of a US application filed on Dec. 26, 1978, published on Jul. 9, 1980. This application has been filed in the name of Monsanto Company, St. Louis, Mo., USA.

This application describes on page. 1, lines 5-6, vinyl chloride polymer films and plastisoles for use in the preparation of such films.

On page 2, first two lines, plasticisers are mentioned for the preparation of such plastisoles, being esters of carboxylic acids, such as for example alkyl benzyl phthalates. On page. 3, lines 16-18, the use of a plasticising amount of for example a di-ester is mentioned, selected from alkyl benzyl succinates.

On pag. 6, lines 7-18, these alkyl benzyl succinates are further discussed.

Here is mentioned that the di-esters of succinic acid are formed by linking a benzyl radical directly to the one carboxyl group, and an alkyl radical to the other carboxyl group of the acid, for example succinic acid.

On line 18, in decreasing sequence of preference, examples of such alkyl compounds are enumerated, six in total.

These relate to isobutyl, n-butyl, sec-butyl, neopentyl, isopropyl and isoamyl respectively.

The alkyl compounds enumerated here thus have 4, 4, 4, 5, 3 and 5 carbon atoms.

PROBLEM TO BE SOLVED AND AIM OF THE INVENTION

Still today there is an enormous attention and research for novel plasticisers. Because the traditional (ortho-) phthalate esters are under pressure in view of their toxicity and their environmental impact, alternative compounds are highly desired. The industry intensively searches for alternatives for these (ortho-) phthalate esters. However, these alternatives in most cases exhibit a number of negative properties compared to the phthalate esters. In particular as regards specific applications such as the quick fusing products described herein, the possibilities are limited.

The problem with the compounds as described above in the state of the art resides in the fact that when used as plasticiser its properties as quick fusing plasticisers combined with a low VOC (degree of volatility, Volatile Organic Compound) are insufficient. The aim of the present invention is to meet these drawbacks by the synthesis and the marketing of suitable succinates, and on top hereof to meet the ever-increasing requirements of an ecological nature.

The aim of the present inventors is the synthesis and the marketing of a new series of products that are quickly fusing or jellifying, but apart hereof preferably are made of raw materials of biological origin.

The aim of the invention consequently is the development of innovative relevant new plasticisers having as well quick fusing properties as well as low volatile properties (VOC).

DESCRIPTION OF THE INVENTION

The invention relates to plasticisers for a thermoplastic polymer, comprising a succinate mixed ester of benzyl on the one part, and branched nonyl or decyl on the other part. More specific embodiments of the invention are set forth in the annexed dependant claims, as well as in the description of the preferred embodiments of the invention that follows.

DETAILED DESCRIPTION OF THE INVENTION

Definitions

The term 'a di-ester based on succinic acid' in the context of the present invention is meant to be a chemical compound, whereby both acid functions of the succinic acid are esterified and whereby these ester groups either have the same chemical structure or have a different chemical structure.

The term 'mixed ester' in the context of the present invention is meant to be a chemical compound as described above and whereby the ester groups of the di-ester have a different chemical structure or are asymmetrical. In the text set forth hereinafter, mixed esters sometimes are denoted as asymmetrical esters, resp. asymmetrical succinates.

The term 'succinate mixed ester' is meant to be the same as the term 'mixed ester based on succinic acid'.

The term 'plastisole' in the context of the present invention is meant to be a suspension of polymers, preferably thermoplastic polymers, further preferably polyvinylchloride, in a plasticiser. Such a plastisole flows like a liquid and can be poured in a mould for heating and formation of an end product as a plastic. In case the components in the mould are heated to high temperature, for example around 177 Celsius, the polymer and the plasticiser melt and fuse with each other. When hereupon the form is cooled again, for example till 60 Celsius, a flexible plastic is created wherein the plasticiser is incorporated in a permanent manner.

Apart from the above-mentioned application in a form or mould, a plastisole can also be used as textile ink for silk-screen printing and as a coating, in particular for outdoor or outside applications (as roofing material, furniture and dip-coating).

The term 'composition' in the context of the present invention is meant to be a process for the preparation of plastic formulations by mixing polymers as for example PVC, polypropylene, SEBS, PVB, PLA or comparable compounds with additives such as for example esters, mineral oils or similar compounds in liquid form. There are various critical criteria for obtaining a homogeneous mixture of the various raw materials. The mixing process itself, as well as the application of heat, is important factors. Co-kneaders and twin-screws that work in opposite as well as in the same direction, as well as internal mixers are the most widely used apparatus for the mixing of raw materials, as applied in the plastics industry.

For S-PVC one should take into account that often, prior to the mixing- or composition-step, the plasticiser concerned is mixed with the PVC in powdery form, so as to allow a rapid absorption of the plasticiser. As soon as the absorption has taken place, the mixture is loaded into the compounder and under the influence of heat an intimate blending takes place. The absorption of liquids of various natures by polymers at increased temperatures, but below the melting temperature of the polymer, is not an unusual process in the industry as mixing/absorption process step.

Under the term 'thermoplastic polymer' in the context of the present invention is meant a material made out of plastic that weakens upon strong heating. This is contrary to thermoset plastic materials that remain firm upon heating.

This materials group comprises linear macromolecules without transverse bonds (although in some cases a branching may occur).

Elastomers such as rubbers are a particular subclass of the thermoplastic polymers.

Examples of thermoplasts are polyvinylchloride (PVC), polypropylene (PP), Teflon and polymethylmethaacrylate (PMMA).

The term 'quick fusing' in the context of the present invention is meant to describe the situation whereby in case of mixing of a plasticiser and a polymer in a plastisole, the polymer concerned and the plasticiser quickly blend into each other, or intimately fuse. In this chemical integration process the viscosity of the mixture increases, and in principle the faster this process takes place, the more efficient is the working of the plasticiser on the polymer.

The term 'cold flex' in the context of the present invention is meant to denote the glass transition temperature of the polymer or compound concerned. The aim is to keep this cold flex as low as possible, because the material concerned under this temperature becomes brittle or fragile, and as a result hereof becomes unsuitable for common applications.

Preparation Method of the Plasticisers:

The plasticisers according to the invention may be prepared starting from on the one part succinic acid, on the other part selected alcohols as starting materials.

The molar ratio between the selected alcohols may be chosen so as to obtain an optimal product from the point of view of compatibility with the polymer with which the plasticiser will be processed up to a plastisole or a plastic, for example PVC. A molar ratio ranging from 0.3-0.7 to 0.7-0.3 is suitable.

More specifically in a number of cases a molar ratio of 0.5-0.5 is regarded as optimal.

The synthesis may then be performed along the following lines.

First a mixture is made of the selected alcohols in the correct concentration, depending on the application. These alcohols are put in a reactor, whereupon they are heated to approximately 90° C. Hereupon succinic acid is added such that the molar ratio of acid over alcohol is around 1:2. A small excess amount of alcohol may be desired to complete the reaction. As catalyst for example a strong acid like sulphuric acid is added. The reaction is stopped when no further water is formed. After neutralisation of the catalyst the possible excess amount of alcohol can be removed by distillation. The mixture may be washed at various stages to eliminate possible impurities. Hereupon the product is dried by heating up to elevated temperatures (80 à 150° C.) under the application of vacuum.

EXAMPLE 1

Composition of a Mixed Ester of Benzyl Alcohol on the One Part and 2-Propylheptanol on the Other Part with a Molar Ratio of 0.5-0.5

The mixed ester of benzyl alcohol and 2-propyl alcohol is prepared by esterification with an alcoholic mixture.

According to an alternative preparation method this mixed ester may also be prepared starting from benzyl chloride and 2-propylheptanol in the same molar ratio as set forth above, and succinic acid anhydride.

EXAMPLE 2

Composition of a Mixed Ester of Benzyl Alcohol on the One Part and Isononyl-Alcohol on the Other Part with a Molar Ratio of 0.5-0.5

The preparation process proceeds along the same lines as set forth above in Example 1.

Preparation Method of the Plastisole:

In a next step of the process the plasticisers prepared according to the examples set forth above are used for the synthesis of plastisole samples. In this step the various plasticisers are mixed with PVC. The various plasticisers described in the examples are used in the preparation of PVC samples as well in transparent as in foaming formulations.

Evaluation of the Properties (Transparent Formulation):

Two classical plasticisers based on esterified succinic acid are compared with a reference plasticiser diisononylphthalte (DINP) and with the asymmetrical benzyl-(2-propylheptyl) succinate according to the invention. The two classical symmetric aliphatic esters on the basis of succinic acid are on the one part diisononyl succinate (DINS) and on the other part di-(2-propylheptyl) succinate (DPHS). Their plasticising behaviour is compared in a plastisole based transparent PVC film.

For the transparent formulation the following ingredients are used:

(flooring type, top layer): Solvin 382NG 100 phr (obtainable from Solvay S.A., Belgium), plasticiser 50 phr, Ca/Zn stabiliser (Baerostab NT 306) 2.5 phr (obtainable from the company Baerlocher).

The transparent film so formed is subjected to amongst others a weight loss test (volatility) at 100° C. for respectively 4 and 7 days. The plasticiser efficiency is determined by means of a hardness measurement. A measure for the compatibility of the plasticiser is the transparency. The results of these tests are summarized in the table below.

Summary of the results of the comparative studies of di-alkyl-succinates with di-isononylphthalate and an asymmetrical benzyl-2-(2-propyl heptyl) succinate.

TABLE 4

Comparative study di-alkyl phthalate, dialkyl succinate and benzylalkyl succinate:

| Property | Parameter | | DINP (ref.) | DINS | delta vs. ref. | DPHS | delta vs. ref. | BPHS (Pure) | delta vs. ref. |
|---|---|---|---|---|---|---|---|---|---|
| Volatile | Weight difference @ 100° C. | After 4 days (%) | −2.30% | −17.40% | ×7.6 | −11.50% | ×5.0 | −10.80% | ×4.7 |
| | | After 7 days (%) | −4.00% | −24.50% | ×6.1 | −17.60% | ×4.4 | −17.40% | ×4.35 |
| Efficiency | Stiffness | Shore A | 81 | 82 | −1.2% | 87 | −7.4% | 74 | 8.6% |
| Compatibilty | Transparency | % Transparent | 88.30% | 77.60% | −12.12% | 58.10% | −34.20% | 87.10% | −1.36% |

Legend:
DINP: diisononylphtalate
DINS: diisononylsuccinate
DPHS: di-(2-propylheptyl)succinate
BPHS: benzyl-(2-propylheptyl)-succinate From the above table one may conclude that the compatibility and the plasticising efficiency of diisononyl succinate and di-(2-propylheptyl) succinate with a PVC polymer are in the range from not good to very bad.

It is surprising in this study that the benzyl-alkyl molecule (in case BPHS) has a remarkably better efficiency (lower Shore A) as compared to the reference plasticiser, but it also has a substantially better Shore A (13 Shore A points) as compared tot the more obvious di-(2-propylheptyl) succinate ester. Also from another similar comparative test (Table 2) we may note that in particular BINS and BPHS show an improvement of respectively +8.75% and 6.25% in Shore A hardness as compared to the reference DINP (Table 2). This is in line with the result in the above table 4.

Also the transparency of the BPHS in this test is excellent and quasi-identical to the reference plasticiser, but substantially better than the transparency of the two symmetrical alkyl succinates DINS and DPHS. This points to a non-compatibility of the last two plasticisers with respect to the polymer matrix.

On the basis of the examples and the results from the tables 2, 3 and 4 we may conclude that with the asymmetrical benzyl-alkyl succinate esters we have at our disposal a series of fast, efficiently jellifying plasticisers, with excellent compatibility and efficient plasticising property without the extreme volatility that is usually linked to extremely fast fusing plasticisers.

Apart from the above, the benzyl-alkyl plasticiser family shows good till very good cold flex properties.

Evaluation of the Results (Foaming Formulation):

The following ingredients were used for the foaming formulation: (flooring type, foaming layer): Solvin 367NK 100 phr (obtainable from Solvay S.A., Belgium), plasticiser 62 phr, CaCo3 (15μ) Porofor ADC (50%) (This is a blowing agent obtainable from the company Lanxess AG, Germany)+ DINP (50%) 5 phr, Baerostab KK42 2.0 phr (obtainable from the company Baerlocher).

(The abbreviation phr is a term known for the person skilled in the art: it indicates the amounts (in weight percentages) of the ingredients used, en denotes parts per hundred parts of resin).

As is apparent from the above examples, a plastisole usually comprises a thermoplastic polymer, a primary (as well as possibly a secondary) plasticiser, and usually a stabiliser. To this mixture other ingredients may be added, such as pigments and the like.

After the preparation of the above plastisoles, an evaluation of the properties took place. The following parameters were measured from the transparent formulation:

(1) on the paste⇒ viscosity, paste aging, jellifying behaviour, air removal from the plastisole as prepared, thermal stability.
(2) On the films as prepared the following parameters were measured: colour, gloss, weight loss, water absorption and migration of plasticiser.

From the foaming formulation, the following parameters were measured:

(1) On the paste⇒ viscosity and paste aging.
(2) On the foaming samples⇒ density, expansion speed, cell quality and colour (yellow index).

The results of the evaluation of these products were compared with the results of the evaluation of the various reference materials or commercial benchmarks such as DOP, DINP, DIDP, DOTP, DINCH and DOA.

From the comparison of these results is appears clearly that plasticisers comprising a succinate mixed ester of benzyl on the one part and branched nonyl or decyl on the other part are more suited, specifically because they better combine the properties of fast fusing plasticisers with the property of a low VOC (volatility) behaviour.

As set forth above, the invention thus relates to a class of new plasticisers, based on succinic acid, for use in amongst others polyvinylchloride, PVC co-polymer and polar rubbers.

The plasticisers are made from raw materials with the possibility to produce up to 100% bio plasticisers.

The new plasticisers combine an optimal compatibility with excellent thermal and light stability. The products may be used as primary plasticiser that renders the necessary flexibility to the products, but also as secondary plasticisers to improve certain properties. High fusing products according to the invention so may be added to standard plasticisers to fasten the fusing or jellifying.

Further Experimental Results

In further experiments performed by the inventors, emphasis has been laid on the benzyl-alkyl esters and more in particular the succinates esterified with benzyl alcohol on the one part and a branched C9 or C10 alcohol (isononyl or isodecyl alcohol). More in particular the experiments have been focussed on the following two molecules:

Benzyl-isononyl succinate (hereinafter abbreviated to BINS)
Benzyl-(2-propylheptyl) succinate (hereinafter abbreviated to BPHS)

Extensive comparative tests were performed between classical "general purpose", classical "fast fusing" and classical "cold flex" plasticisers and three benzyl-alkyl plasticisers.

The laboratory wherein such experiments were performed is a state-of-the-art lab, and as a result the results so obtained may be regarded as a technically objective criterion. In table 1 the various plasticisers of the study are set forth.

In tables 2 and 3 the tests and results for a plastisole PVC process on the one part and for a thermoplastic PVC dry-blend compound process on the other hand are set forth.

TABLE 1

Molecules of the comparative study succinates versus existing plasticisers.

| ID | Component (Molecule) | Code | Composition (Based on GC) |
|----|---------------------|------|--------------------------|
| 1 | Benzyl-2-ethylhexyl succinate | BEHS | ~20% DiBnSu; ~51% BEHS; 29% DiEHSu |
| 2 | Benzyl-isononyl-succinate "pure" | BINS | ~98.3% BINS |
| 3 | Benzyl-isononyl-succinate "Blend 1" | BINS - 50 | ~30% DiBnSu, ~50% BINS, ~20% DiINSu, |
| 4 | Benzyl-isononyl-succinate "Blend 2" | BINS - 75 | ~10% DiBnSu, ~40% BINS, ~50% DiINSu |
| 5 | Benzyl-(2-propylheptyl)-succinate "pure" | BPHS | ~3% DiBnSu; 93% BPHS; ~3% DiINSu |
| 6 | Benzyl- (2-propylhepty)l-succinate "Blend 1" | BPHS - 50 | ~20% DiBnSu; ~47% BPHS; ~29% DiPHSu |
| 7 | Benzyl-Propylheptyl-succinate "Blend 2" | BPHS - 75 | ~6% DiBnSu; ~36% BPHS; ~54% DiPHSu |
| 8 | Di-isononylphthalate | DINP | Ref. 1/General purpose Plasticizer |
| 9 | Di-octyltherephthalate | DOTP | Ref. 2/General Purpose Plasticizer |
| 10 | Di-octyladepate | DOA | Ref. 3/Cold Flex Plasticizer |
| 11 | Isononyl Benzoate | INB | Ref. 4/Fast Gellator in Plastisole applications |

Legend:
GC: Gas Chromatography
DiEHSu: Di-(2-ethylhexyl) succinate;
DiPHSu: Di-(2-propylheptyl) succinate;
DiBnSu: Di-benzyl succinate;
DiINSu: Diisononyl succinate;

TABLE 2

Results of the plastisol

Plastisol Test Results:

| | | Gelation (Visc. vs. Temp.) | viscosity after 24 h 100 phr PVC, 50 phr Plasticizer, 3 phr ESBO, | Thickening | Extractions by H$_2$O (Weight Difference %) | | | | Plasticize Efficiency | |
|---|---|---|---|---|---|---|---|---|---|---|
| ID | Code | | 2 phr Ca/Zn Stab. | | 1 d | 7 d | dry | Shore A | % Difference vs. DINP | % Difference vs. DOA |
| 1 | BEHS | superfast | signif. lower | higher | 0.1 | −2.15 | −3.9 | 73 | 8.75% | 2.67% |
| 2 | BINS | faster | signif. lower | slightly higher | 0.8 | 1.5 | 0.1 | 73 | 8.75% | 2.67% |
| 3 | BINS - 50 | faster | signif. lower | slightly higher | 0.3 | −1.4 | −2.9 | 76 | 5.00% | −1.33% |
| 4 | BINS - 75 | equal | signif. lower | slightly higher | 0.8 | 1.1 | −0.4 | 72 | 10.00% | 4.00% |
| 5 | BPHS | faster | signif. lower | slightly higher | 1 | 1.8 | 0.2 | 75 | 6.25% | 0.00% |
| 6 | BPHS - 50 | faster | signif. lower | slightly higher | 0.4 | −1 | −2.5 | 76 | 5.00% | −1.33% |
| 7 | BPHS - 75 | slower | signif. lower | slightly higher | 0.8 | 0.9 | −0.7 | 79 | 1.25% | −5.33% |
| 8 | DINP | reference | reference | reference | 0.8 | 1.8 | 0.7 | 80 | reference | −6.67% |
| 9 | DOTP | slower | reference | less high | 0.8 | 1.7 | 0.7 | 83 | −3.75% | −10.67% |
| 10 | DOA | slower | signif. lower | slightly higher | 1 | 2.1 | 0.7 | 75 | 6.25% | reference |
| 11 | INB | faster | signif. lower | higher | 0.9 | 1.9 | 0.5 | 73 | 8.75% | 2.67% |

TABLE 3

Results of the dry blending

Thermoplastic Application (Dry Blend/Compound)

| | | Dry Blend Process efficiency (mixing time/67 phr formula) | | | Plasticize Efficiency (Shore A/67 phr formula) | | Compression Moulded sheets (67 phr and 33 phr data) | | | |
|---|---|---|---|---|---|---|---|---|---|---|
| ID | Code | 67 phr formula (# min. to dry blend) | x times faster processing vs DINP | x times faster versus DOA | Shore A | % better vs. DINP | Cold Flex via Tg (67 phr) | Delta versus DINP (%) | Cold Flex via Tg (33 phr) | Delta versus DINP (%) |
| 1 | BEHS | 1.57 | 3.7 | 3.2 | 68 | 5.6% | −49.7 | 8.0% | −19.3 | 68% |
| 2 | BINS | 2.2 | 2.6 | 2.3 | 69 | 4.2% | −50.7 | 10.2% | −24.8 | 116% |
| 3 | BINS - 50 | 1.87 | 3.1 | 2.7 | 69 | 4.2% | −51.1 | 11.1% | −22.1 | 92% |
| 4 | BINS - 75 | 3.67 | 1.6 | 1.4 | 69 | 4.2% | −59.9 | 30.2% | −33.5 | 191% |
| 5 | BPHS | 3.1 | 1.9 | 1.6 | 68 | 5.6% | −51.7 | 12.4% | −23 | 100% |

TABLE 3-continued

Results of the dry blending

Thermoplastic Application (Dry Blend/Compound)

| | | Dry Blend Process efficiency (mixing time/67 phr formula) | | Plasticize Efficiency (Shore A/67 phr formula) | | Compression Moulded sheets (67 phr and 33 phr data) | | | |
|---|---|---|---|---|---|---|---|---|---|
| | | 67 phr | x times | | | (67 phr) | Delta | (33 phr) | Delta |
| ID | Code | formula (# min. to dry blend) | faster processing vs DINP | x times faster versus DOA | Shore A | % better vs. DINP | Cold Flex via Tg | versus DINP (%) | Cold Flex via Tg | versus DINP (%) |
| 6 | BPHS - 50 | 2.93 | 2.0 | 1.7 | 70 | 2.8% | −52.5 | 14.1% | −22.6 | 97% |
| 7 | BPHS - 75 | 4.1 | 1.4 | 1.2 | 70 | 2.8% | −58.9 | 28.0% | −22.9 | 99% |
| 8 | DINP | 5.8 | reference | 0.9 | 72 | reference | −46 | reference | −11.5 | reference |
| 9 | DOTP | 7 | 0.8 | 0.7 | 74 | −2.8% | −41.4 | −10% | −10.9 | −5% |
| 10 | DOA | 5.1 | 1.1 | reference | 63 | 5.6% | −72.5 | 58% | −48.1 | 318% |
| 11 | INB | | | | | not applicable | | | | |

From the above experiments and tables the following conclusions may be drawn:

Comment of the Results of Table 2:

Various plastisoles were prepared on the basis of various plasticisers set forth in Table 1, according to the following formulae:

100 phr PVC (Vestolit B7021 ultra), 50 phr Plasticiser (Table 1), 3 phr ESBO (Drapex 39) (acting as anti-oxydans), 2 phr Ca/Zn stabiliser (Mark CZ 149).

On these plastisoles the increase of viscosity over temperature was determined by means of a rheology meter, so as to determine amongst others the "jellifying" behaviour and the fusion behaviour of the suspension: gelation curve (Temperature/Viscosity curve).

Apart from the above, the viscosity property of the plastisole solution was determined after 24 h (viscosity vs. Shear) and the thickening was determined. Apart from this the extraction of the plasticiser in water (expressed as % weight gain/weight loss) after 1 day, 7 days were determined, as well as after drying the sample.

The effectiveness of the plasticiser on the stiffness after processing is determined by means of a Shore A hardness measurement. Films are prepared by means of a Mathis furnace at 200° C. for 2 minutes and 1 mm thickness to complete the mechanical properties (tensile/elongation) and the hardness of the film.

Surprisingly the plasticisers on the basis of the asymmetrical esters in pure or mixed form, on the basis of benzyl-isononyl succinate (BINS), benzyl(2-propylheptyl) succinate (BPHS) and the benzyl-ethylhexyl succinate (BnEHSu) are very efficient plasticisers compared to the "general purpose" Di-isononylphtalate (DINP) and di-octyl terephthalate (DOTP) esters.

On top hereof the pure benzyl-isononyl succinate (BINS), benzyl-propylheptyl succinate (BPHS) also appear to be more efficient plasticisers compared to the known di-octyl-adipate ester (DOA).

On top hereof, surprisingly, in particular the pure benzyl-isononyl succinate (BINS) and the pure benzyl-propylheptyl succinate (BPHS) appear to show a very good (very low) water solubility profile compared to the reference molecules.

On top hereof all, and certainly the two asymmetrical esters BINS and BPHS appear to stand the comparison test with isononyl benzoate (INB) as regards efficiency, without showing the extremely high volatility of INB. INB is 4 to 5 times more volatile, as pure compound, as compared to the pure compounds BINS and BPHS.

The volatility of these compounds is determined by means of a thermal-gravimetrical analysis; in this case the product is heated to 200 Celsius during approx. 10 minutes, and the loss of weight is determined; expressed as mass % this yields the following results for the 3 molecules: −61.7 m−% vs.−15.1 m−% and −12.9 m−%. In Table 5 an overview of the various molecules can be found.

For all of the abovementioned compounds the weight loss is shown in the table 5 set forth below. In this table it is clearly illustrated that the weight loss for the compounds according to the invention is three to four times less than for the super fast-fusing light compounds as for example INB and they are less volatile than DOA:

TABLE 5

Table of volatility of various molecules:

| ID | Code | Volatily plasticizer (weightloss [m %]) (200° C./10 min) |
|---|---|---|
| 1 | BEHS | −19.2 |
| 2 | BINS | −15.1 |
| 3 | BINS - 50 | −13.3 |
| 4 | BINS - 75 | −17 |
| 5 | BPHS | −12.9 |
| 6 | BPHS - 50 | −13.5 |
| 7 | BPHS - 75 | −13.5 |
| 8 | DINP | −4.3 |
| 9 | DOTP | −4.8 |
| 10 | DOA | −18.4 |
| 11 | INB | −61.7 |

From the above data it can be concluded that asymmetrical esters based on succinic acid of the type "benzyl-alkyl", whereby the branched alkyl comprises at least 9 or 10 carbon atoms, are particularly effective and efficient plasticisers for plastisole based applications (fast fusing, low water solubility, high elasticity).

From the above it may also be concluded that the molecules benzyl-isononyl succinate and benzyl-propylheptyl succinate as such can be used as primary plasticiser for plastisole applications. However, these plasticisers can also be combined as fast fusing plasticisers as co-plasticisers with known slow fusing general purpose plasticisers of the type phthalate or terephthalate esters with C8 or higher alkyl groups such as di-(2-ethylhexyl) phthalate DEHP or DOP), di-isononyl phthalate (DINP), di-(2-propylheptyl) phthalate (DPHP), di-(2-ethylhexyl) terephthalate (DEHT or DOTP), di-isononyl terephthalate (DINTP), di-(2-propylheptyl) terephthalate (DPHTP), of the type cyclohexane di-carboxylate ester with C8 or higher alkyl groups such as di-isononyl-1,2-cyclohexane di-carboxylate (DINCH), di-(2-propylheptyl) 1,2-cylcohexane dicarboxylate (DPHCH), of the type 2-ethylhexyl epoxy stearate, isononyl epoxy stearate. The latter compounds are known to jellify slower as compared to the reference molecules DINP from table 2.

Comment on the Results of Table 3:

Various sheets are squeezed from a compound of the following composition: 100 phr PVC (Solvin 5271 PC); 33 phr/67 phr Plasticizer (table 1); 3 phr ESBO (Drapex 39); 2 phr Ba/Zn-Stabiliser (Mark BZ965); 0.4 phr Processing aid (Ca Stearate). First by means of a mixer a dry blend is prepared at 88° C. (30 min). At 165° C. for 5 minutes a compound is prepared (on a Brabander) for finally squeezing the sheets at 170° C. The process of mixing is evaluated (the time required to arrive at a dry blend) and also on the sheets so produced a number of parameters is determined such as the hardness of the sheets (Shore A) and the glass transition temperature (Tg). The values are compared to each other and with the reference plasticisers.

Surprisingly all asymmetrical esters in pure or mixed form, on the basis of Benzyl-isononyl succinate (BINS), benzyl-(2-propylheptyl) succinate (BPHS) and Benzyl-ethylhexyl succinate (BnEHSu) give rise to a mixing time that is 1.4 to 3.7× times faster as compared to the reference plasticiser DINP and certainly as compared to the still less efficient plasticiser DOTP. This is particularly significant and relevant for the PVC compounders that can attain a substantially increased efficiency increase. Even compared to DOA there is still a production efficiency increase for all succinate compounds, but a remarkable improvement of at least 1.6 times up to 2.3 times for the pure asymmetrical esters benzyl-isononyl succinate and benzyl-(2-propylheptyl) succinate. Apart hereof the plasticiser efficiency for all succinates is at least as good or even substantially better for all succinates as compared to the reference DINP.

Finally, and very surprising in particular at low concentrations of the succinate plasticisers (33 phr), is the fact that the Tg is approximately twice as low as the Tg of the reference molecule DINP. This opens perspectives for outdour applications. At high concentrations (67 phr) this still is 8% up to 30% better than the reference molecule. Finally, not shown in Table 3, the extraction of the pure plasticisers BINS and BPHS by means of water is very good and better than the reference DINP, DOTP and DOA. This is in line with the comparable water extraction test from table 2.

From the results of table 3 it further may be concluded that the molecules benzyl-isononyl succinate and benzyl-(2-propylheptyl) succinate as such can be used as primary plasticisers for dry-blend-compounding thermoplastic applications with PVC. Apart from the above, these compounds can also be combined as co-plasticiser (blend) with known slow absorbing general plasticisers so as to speed up the mix and compounding process on the one part, and to improve the cold flexibility of the final product on the other hand. The envisaged slow plasticisers are then typically of the type Phthalate of Therephthatale esters with C8 or higher alkyl groups such as di-(2-ethylhexyl)phthalate (DEHP also called DOP); di-isononyphthalate (DINP); di-(2-propylheptyl) phthalate (DPHP); di-(2-ethylhexyl)therephthalate (DEHT also called DOTP); di-isononytherephthalate (DINT); di-(2-propylheptyl) therephthalate (DPHTP). The esters of the type cyclohexane dicarboxylate ester with C8 of higher alkyl groups such as diisononyl-1,2-cyclohexanedicarboxylate (DINCH); di-(2-propylheptyl) 1,2-cyclohexanedicarboxylate (DPHCH) and of the type alkyl epoxy stearate such as for example 2-ethylhexyl epoxy stearate (Proviplast PLS Green 8); isononyl epoxy stearate (Proviplast® PLSGreen 9); it is known that these types of esters absorb slowly up to very slowly, but they show a more than acceptable good (low) Tg as compared to DINP; the latter characteristic makes these compounds suitable for low temperature applications. The mix with the asymmetric succinates of the type benzyl-isononyl succinates and benzyl-propylheptyl succinates would yield in particular a production efficiency apart from a good cold flex.

The most important technical advantage of the plasticisers according to the invention resides in the fact that two characteristics are combined in these molecules. On the one part the plasticisers according to the invention show a sufficiently low volatility or VOC, but on the other hand they show a very good fast fusing/good absorption property; this characteristic results in an outstanding plasticising behaviour. This invention describes products that by a combination in the correct ratio combine these two characteristics in one new and innovative molecule.

The branched alcohols may be choses from isononanol or isodecanol but also all possible isomers and mixtures of these products.

This invention describes the use of these products as plasticisers. The choice of the alcohols is crucial such that the ester as prepared shows an outstanding plasticising property. Also the products are chosen as plasticiser for PVC but also for other possible compatible polymers such as PVC copolymers, polyester, polyvinylbutyral, polar rubbers or polyurethane.

The invention claimed is:

1. A plasticizer for a thermoplastic polymer, comprising a succinate mixed ester of benzyl-2-propylheptyl-succinate or benzyl-isononyl-succinate.

2. The plasticizer according to claim 1, further comprising a di-ester of di-benzyl succinate or di-nonyl succinate or di-decyl succinate.

3. The plasticizer according to claim 2, wherein the mixed ester comprises at least 30 mol % of the total amount of succinates.

4. A plastisol, comprising a thermoplastic polymer and the plasticizer according to claim 1.

5. The plastisol according to claim 4, comprising the plasticizer according to claim 1 as primary or secondary external plasticizer.

6. The plastisol according to claim 4, wherein the thermoplastic polymer is selected from the following: polyvinyl chloride, polyvinyl butyral, polyurethane, polyester, polyvinyl alcohol emulsions, polar rubber or a polyvinyl chloride rubber copolymer, or a combination of two or more of said polymers.

7. The plastisol according to claim 4, wherein the thermoplastic polymer is selected from the following polymers: polylactic acid, polybutene succinate, polyhydroxy alkanoate, cellulose derivatives, polyvinyl chloride, polyvinyl butyral, polyurethane, polyester, polyvinyl alcohol emulsions, polar rubber or a polyvinyl chloride rubber copolymer, or a combination of two or more of the polymers.

8. A plastic material comprising a thermoplastic polymer and the plasticizer according to claim 1.

9. A plastic material, comprising a thermoplastic polymer and the plasticizer according to claim 1 as a primary or secondary external plasticizer.

10. The plastic material according to claim 8, wherein the thermoplastic polymer is selected from the following: polyvinyl chloride, polyvinyl butyral, polyurethane, polyester, polyvinyl alcohol emulsions, polar rubber or a polyvinyl chloride rubber copolymer, polylactic acid, polybutene succinate, polyhydroxy alkanoate or cellulose derivatives, or a combination of two or more of said polymers.

11. The plastic material according to claim 9, wherein the thermoplastic polymer is selected from the following: polyvinyl chloride, polyvinyl butyral, polyurethane, polyester, polyvinyl alcohol emulsions, polar rubber, a polyvinyl chloride rubber copolymer, or a biopolymer or a combination of two or more of said polymers.

12. The plastic material according to claim 11, wherein said biopolymer is selected from the following: polylactic acid, polybutene succinate, polyhydroxy alkanoate or cellulose derivatives, or a combination of two or more of said biopolymers.

13. A method for using a succinate mixed ester of benzyl-2-propylheptyl-succinate or benzyl-isononyl-succinate as a plasticizer in a thermoplastic polymer comprising the step of adding said succinate mixed ester to said thermoplastic polymer.

14. The method for using the succinate mixed ester according to claim 13 as a plasticizer along with a thermoplastic in a plastisol comprising the step of adding said succinate mixed ester to said thermoplastic polymer.

15. The method for using the succinate mixed ester according to claim 13 as a plasticizer in a plastic material comprising the step of adding said succinate mixed ester to said thermoplastic polymer.

* * * * *